United States Patent [19]

Ward et al.

[11] Patent Number: 5,346,896
[45] Date of Patent: Sep. 13, 1994

[54] 1-(ARYL OR HETEROARYL)-4[ω-(ARYL OR HETEROARYL)ω-(ARYL OR HETEROARYL)ALKYLENE]PIPERAZINES

[75] Inventors: Terence J. Ward, Reading; Graham J. Warrellow, Stanmore, both of England

[73] Assignee: John Wyeth & Brother, Limited, Maidenhead, United Kingdom

[21] Appl. No.: 867,221

[22] PCT Filed: Oct. 1, 1991

[86] PCT No.: PCT/GB91/01693
§ 371 Date: Jun. 3, 1992
§ 102(e) Date: Jun. 3, 1992

[87] PCT Pub. No.: WO92/06082
PCT Pub. Date: Apr. 16, 1992

[30] Foreign Application Priority Data

Oct. 3, 1990 [GB] United Kingdom ............... 9021535

[51] Int. Cl.⁵ .............. A61K 31/495; C07D 295/088; C07D 401/06; C07D 403/06
[52] U.S. Cl. .................... 514/252; 514/253; 514/254; 514/255; 544/295; 544/296; 544/357; 544/360; 544/363; 544/364; 544/366; 544/370; 544/371; 544/392; 544/394
[58] Field of Search ............... 544/357, 360, 364, 363, 544/370, 371, 392, 394, 295, 366, 296; 514/252, 254, 253, 255

[56] References Cited

U.S. PATENT DOCUMENTS

| | | | |
|---|---|---|---|
| 4,080,453 | 3/1978 | Nishimura et al. | 544/392 |
| 4,705,855 | 11/1987 | Desideri et al. | 544/370 |
| 5,177,078 | 1/1993 | Ward et al. | 544/370 |

FOREIGN PATENT DOCUMENTS

| | | |
|---|---|---|
| 0054974 | 6/1982 | European Pat. Off. |
| 0321131 | 6/1989 | European Pat. Off. |
| 0382636 | 8/1990 | European Pat. Off. |

OTHER PUBLICATIONS

Nishimura et al, *Chemical Abstracts*, vol. 87, No. 53381 (1977).
Nishimura et al, *Chemical Abstracts*, vol. 87, No. 53383 (1977).
Akopyan, Zh. G., et al., Chem. Abst. 71:13091w (1968).
Vinay, S. et al., Indian J. Pharm. vol. 39 (2), 35–36 (1977).
Kapil, R. S. et al., Indian J. Chem. vol. 4 (4) 177–187 (1966).

*Primary Examiner*—Emily Bernhardt
*Attorney, Agent, or Firm*—Arthur G. Seifert

[57] ABSTRACT

Disclosed herein are piperazine derivatives of the formula

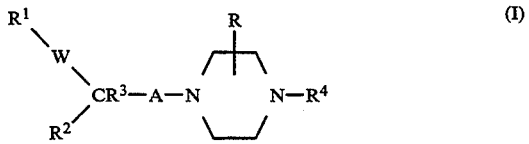

or a pharmaceutically acceptable acid addition salt thereof, wherein
W is $(CH_2)_m$, CHOH or O,
m is one of the integers 1 or 2,
A is an alkylene chain of 1 to 3 carbon atoms optionally substituted by one or more (lower)alkyl groups,
R is hydrogen or lower alkyl,
$R^1$ and $R^2$ are each, independently, aryl or heteroaryl radicals with the proviso that $R^1$ is not an optionally substituted indolyl radical,
$R^3$ is hydrogen or lower alkyl and
$R^4$ is an aryl or heteroaryl radical.

The compounds are $5HT_{1A}$ binding agents which may be used, for example, in the treatment of CNS disorders such as anxiety.

6 Claims, No Drawings

1-(ARYL OR HETEROARYL)-4[ω-(ARYL OR HETEROARYL)ω-(ARYL OR HETEROARYL)ALKYLENE]PIPERAZINES

This invention relates to piperazine derivatives, to processes for their preparation, to their use and to pharmaceutical compositions containing them. The novel compounds act upon the central nervous system by binding to 5-HT receptors (as more fully explained below) and hence can be used as medicaments for treating human and other mammals.

The novel compounds of the invention are those of general formula

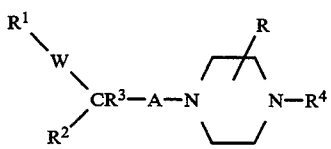

and the pharmaceutically acceptable acid addition salts thereof.

In formula (I):
W is $(CH_2)_m$, CHOH or O,
m is one of the integers 1 or 2,
A is an alkylene chain of 1 to 3 carbon atoms optionally substituted by one or more (lower)alkyl groups,
R is hydrogen or lower alkyl,
$R^1$ and $R^2$ are each, independently, aryl or heteroaryl radicals with the proviso that $R^1$ is not an optionally substituted indolyl radical.
$R^3$ is hydrogen or lower alkyl and
$R^4$ is an aryl or heteroaryl radical. The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, isobutyl, tert-butyl, pentyl and isopentyl.

When used herein "aryl" means an aromatic radical having 6 to 12 carbon atoms (e.g. phenyl or naphthyl) which optionally may be substituted by one or more substituents. For example, when $R^1 R^2$ is aryl it may be a phenyl or naphthyl radical optionally substituted by one or more lower alkyl, lower alkoxy (e.g. methoxy, ethoxy, propoxy, butoxy, cyclopropylmethoxy), halogen, halo(lower)alkyl (e.g. trifluoromethyl), nitro, amino, (lower)alkylamino, di(lower)alkylamino, phenyl, halophenyl, (lower)alkyl phenyl or (lower)alkoxy phenyl substituents. When $R^4$ is aryl it may be, for example, a phenyl or naphthyl radical optionally substituted by one or more of the substituents listed above and/or by one or more hydroxy, hydroxy(lower)alkyl (e.g. hydroxymethyl), —$CONR^5R^6$ (where $R^5$ and $R^6$ are each hydrogen or lower alkyl) or —$NHSO_2$(lower)alkyl substituents. Preferably the aryl radical $R^4$ contains a substituent (e.g. lower alkoxy) in the ortho position. A particularly preferred example of $R^4$ is o-(lower)alkoxyphenyl (e.g. o-methoxyphenyl ) . The term 'heteroaryl' refers to a mono or bicyclic aromatic radical containing one or more hetero ring atoms (e.g. oxygen, nitrogen, sulphur) and which may be optionally substituted by one or more substituents. Preferred examples of substituents for the heteroaryl radicals $R^1$ and $R^2$ are given above for the aryl radicals $R^1R^2$ while preferred examples of substituents for the heteroaryl radical $R^4$ are given above for the aryl radical $R^4$. The heteroaryl radical may for example contain up to 11 ring atoms.

Preferably the heteroaryl radical is a monocyclic radical containing 5 to 7 ring atoms or a bicyclic radical containing 8 to 11 ring atoms. Preferably the hetero ring contains a nitrogen hetero atom with or without further hetero atoms. Examples of heteroaryl groups $R^1$ and $R^2$ are optionally substituted pyridinyl, pyrimidinyl, pyrazinyl, imidazolyl, pyrazolyl, triazolyl and tetrazolyl. These groups may be connected to the remainder of the molecule via a ring heteroatom or a ring C atom.

Examples of the heteroaryl group $R^4$ include optionally substituted pyridinyl, pyrimidinyl, pyrazinyl, quinolinyl or isoquinolinyl.

Preferred compounds have the following substituents either independently or in combination:
(a) W is $CH_2$, CHOH or —O—
(b) A is —$CH_2$—
(c) $R^1$ is aryl, preferably phenyl or substituted phenyl
(d) $R^2$ is phenyl or pyridyl
(e) $R^3$ is hydrogen
(f) $R^4$ is aryl
(g) R is hydrogen The compounds of the invention may be prepared by methods known in the art from known starting materials or starting materials that may be prepared by conventional methods.

One method of preparing the compounds of the invention comprises alkylating a piperazine derivative of formula

with an alkylating agent providing the group

The alkylating agent may be, for example, a compound of formula

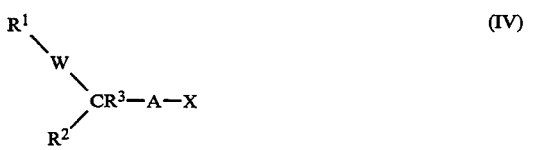

where $R^1$, $R^2$, $R^3$, W and A are as defined above and X is a leaving group such as halogen or an alkyl- or arylsulphonyloxy group. Alternatively the alkylating agent may be an unsaturated compound of formula

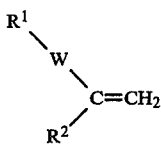
(V)

(where W is $(CH_2)_m$ or O and $R^2$ is an electron withdrawing group e.g. an optionally substituted 2- or 4-pyridyl, 2- or 4-pyrimidyl or 2-pyrazinyl group) and the compound of formula (V) is reacted with the piperazine compound of formula (II) by means of a Michael reaction.

The compounds of formula (I) may also be prepared by reduction of an amide of formula

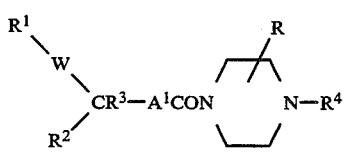
(VI)

where R, $R^1$, $R^2$, $R^3$, $R^4$ and W are as defined above and $A^1$ is an alkylene radical of 1 or 2 carbon atoms optionally substituted by one or more (lower)alkyl groups. The reduction may, for example, be carried out with a hydride transfer agent e.g. boranedimethylsulphide or lithium aluminium hydride. The starting amide of formula (VI) may be made by acylating a piperazine derivative of formula (II) above with an acylating derivative of an acid of formula

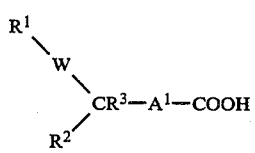
(VII)

The acylating derivative may be, for example, the acid chloride.

Compounds of the invention in which $R^2$ is a heteroaryl group attached via a ring N-atom may be prepared by reacting a heteroaromatic compound of formula $R^2H$ e.g. imidazole with, a compound of formula

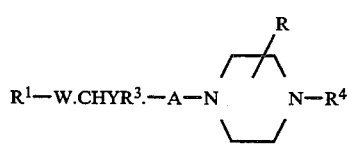
(VIII)

where R, $R^1$, $R^3$, $R^4$ and A are as defined above, W is $(CH_2)_m$ or O and Y is a leaving group such as halogen or an alkyl- or aryl- sulphonyloxy group.

An alternative method of preparing the compounds of the invention comprises arylating or heteroarylating a compound of formula

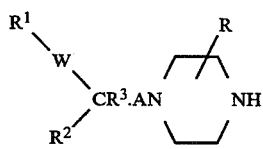
(IX)

where A, R, $R^1$ and $R^2$ are as defined above, W is $(CH_2)_m$ or O and $R^3$ is lower alkyl.

For example the compound of formula (IX) may be reacted with a fluorobenzene compound which is substituted by an electron withdrawing group (e.g. —CHO, cyano, nitro).

Another method of preparing the compounds of the invention comprises reacting a compound having the anion

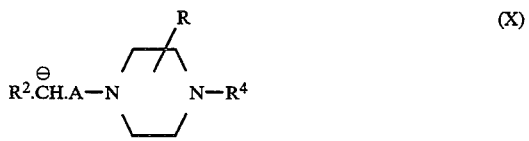
(X)

with a compound of formula

$R^1CHO$ (XIa)

or

$R^1(CH_2)_mY$ (XIb)

where $R^1$ and m are as defined above and Y is a leaving group such as halogen. Reaction of the aldehyde (XIa) with the anion gives a compound of the invention in which W is CHOH while reaction of the compound (XIb) with the anion gives a compound of the invention in which W is $(CH_2)_m$. The anion (X) may be prepared by known methods. For example when $R^2$ is an electron withdrawing heteroaryl radical the anion may be prepared by reacting the compound

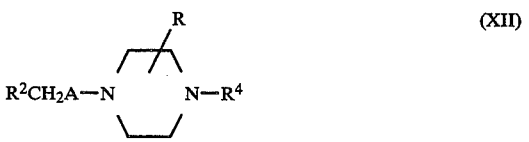
(XII)

with a base e.g. n-butyl lithium.

Compounds of the invention in which W is O may be prepared by reacting a compound having the anion of formula $R^1O^-$ (for example a compound of formula $R^1O$ M where M is an alkali metal) with a compound of formula

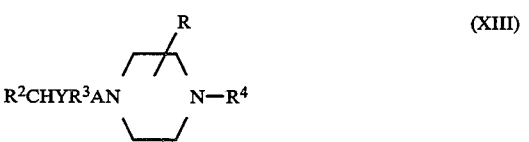
(XIII)

where A, R, $R^2$, $R^3$ and $R^4$ are as defined above, and Y is a leaving group such as halogen or an alkyl- or arylsulphonyloxy group.

Compounds of the invention in which W is $CH_2$ or CHOH may be prepared by reduction of a compound of formula (I) in which W is CO.

Compounds of the invention in which $R^3$ is lower alkyl may be prepared by reacting a compound of the invention in which $R^3$ is hydrogen with a strong base (e.g. butyllithium) and with an alkylating agent (e.g. iodomethane).

If in any of the other processes mentioned herein, a substituent on the group $R^4$ or on the group $R^1$ and/or $R^2$ is other than the one required the substituent may be converted to the desired substituent by known methods. For example, a —CHO substituent may be reduced to hydroxymethyl, a nitro group may be reduced to a amino group which may be sulphonated to give a —NHSO$_2$(lower) alkyl substituent, a cyano group may be hydrolysed to an acid which may be esterified or converted to an amide.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain an asymmetric carbon atom, so that the compounds can exist in different steroisomeric forms. The compounds can be for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. In pharmacological testing it has been shown that the compounds particularly bind to receptors of the 5-HT$_{1A}$ type. In general, the compounds selectively bind to receptors of the 5-HT$_{1A}$ type. Many exhibit activity as 5-HT$_{1A}$ antagonists in pharmacological testing. The pharmacological testing of the compounds indicates that they can be used for the treatment of neuro-psychiatric disorders, such as anxiety and depression in mammals, particularly humans. They may also be useful as hypotensives and as agents for regulating the sleep/wake cycle, feeding behaviour and/or sexual function.

The compounds of the invention are tested for 5-HT$_{1A}$ receptor binding activity in rat hippocampal membrane homogenate by the method of B. S. Alexander and M. D. Wood, J Pharm Pharmacol, 1988, 40, 888–891. 1-(2-Methoxyphenyl)-4-[2-((α-hydroxybenzyl)-2-Pyridyl)ethyl]piperazine, a representative compound of the invention, had an IC$_{50}$ of 20 nM in this procedure.

The compounds are tested for 5-HT$_{1A}$ receptor antagonism activity in a test involving the antagonism of 8-hydroxy-2-(di-n-propylamino)-tetralin (8-OH DPAT) syndrome in the rat.

The invention also provides a pharmaceutical composition comprising a compound or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%. preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution, alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

1-(2-Methoxyphenyl)-4-[2-((α-hydroxy-2-methoxybenzyl)-2-pyridyl)ethyl]piperazine n-Butyl-lithium (1.6M solution in hexane) (7.0 ml, 11.2 mmol, 1.1 equiv.) was added dropwise at below −60° C. to a solution of 1-(2-methoxyphenyl)-4-(2-pyridylethyl)piperazine base (3.00 g, 10.1 mmol) in anhydrous THF (20 ml). The resulting orange-red solution was stirred for a further 0.25 h at −70° C. then quenched with a solution of ortho-anisaldehyde (1.5 g, 11.0 mmol) in anhydrous THF (2 ml). The reaction mixture was poured into water (50 ml) and extracted with dichloromethane (2×75 ml). The organic extract was washed (brine), dried ($Na_2SO_4$) and concentrated in vacuo. The residue was subjected to chromatography ($SiO_2$:$Et_2O$) to give the first $R_f$ diastereoisomer as a white foam which was dissolved in isopropanol (20 ml) and acidified with ethanolic hydrogen chloride to afford the first diastereoisomer of the title compound as the trihydrochloride (227 mg), m.p. 140°–145° C. (Found: C,57.7;H,6.5;N,7.8 $C_{26}H_{31}N_3O_3$.3HCl requires C,57.5;H,6.3;N,7.7%).

The low $R_f$ diastereoisomer was obtained from later fractions which were concentrated in vacuo to white foam, dissolved in isopropanol (15 ml), and acidified with ethanolic hydrogen chloride. The salt slowly crystallised to afford the second diastereoisomer of the title compound as the trihydrochloride isopropanolate (203 mg), m.p. 120°–123° C. (Found: C,58.1;H,7.0:N,7.3. $C_{26}H_{31}N_3O_3$ 3HCl. $C_3H_7OH$ requires C, 57.8; H,6.85;N,7.0%).

EXAMPLE 2

1-(2-Methoxyphenyl) -4-[(2((αhydroxybenzyl)-2-pyridyl)ethyl]piperazine n-Butyl-lithium (1.6M solution in hexane) (2.2 ml, 3.5 mmol, 1.04 equiv.) was added dropwise at below −65° C. to a solution of 1-(2-methoxyphenyl)-4-(2-pyridylethyl) piperazine (1.00 g, 3.36 mmol) in anhydrous THF (15 ml). The solution was stirred for a further 0.25 h at −70° C. then quenched with a solution of benzaldehyde (0.36 g, 3.39 mmol) in anhydrous THF (2 ml). The reaction mixture was poured into water (25 ml) and extracted with dichloromethane (50 ml). The organic extract was washed (brine), dried ($Na_2SO_4$), and concentrated in vacuo to afford an orange-yellow oil (1.1 g). This was subjected to chromatography ($SiO_2$:$Et_2O$) to give the title compound dihydrochloride, three-quarter hydrate (0.81 g) as a 55:45 mixture of diastereoisomers, m.p. 117°–121° C. (Found: C,61.3;H,6.7;N,8.55. $C_{25}H_{29}N_3O_2$.2HCl.075$H_2O$ requires C,61.3;H,6.7;N,8.6%).

EXAMPLE 3

1-(2-Methoxyphenyl)-4-(2-phenoxy-2-phenylethyl)-piperazine (a) 1-(2-Methoxyphenyl)piperazine hydrochloride (9.15 g; 0.04 m) suspended in methylene chloride (150 ml) was treated with diisopropylamine (14 ml) to give a clear solution α-Chlorophenylacetylchloride (6.32 ml; 0.04 m) in methylene chloride (20 ml) was added to the ice cold solution of amines over 20 minutes. The mixture was stirred cold for a further 45 mins, then at ambient temperature for 4 hrs. The solution was washed well with water and dried over $MgSO_4$. The residue of 1-(2-methoxyphenyl)-4-(1-oxo-2-chloro-2-phenylethyl pi- perazine on evaporation was a light brown oil that became a glass on standing.

(b) Sodium hydride 80% dispersion in oil (1.7 g) was added to dry DMF (100 ml) under argon. Phenol (3.76 g; 0.04 m) was added over 20 mins and the resulting grey mixture was stirred a further 20 mins and cooled to 0° C. A solution of 1-(2-methoxyphenyl)-4-(1-oxo-2-chloro-2-phenylethyl)piperazine (13.8 g; 0.04 m) in dry DMF (60 ml) was added over 20 mins. The mixture was heated to 60° C. over a period of about 3 hrs and then maintained at 60° C. for 2½ hrs and then stirred at ambient temperature overnight. The mix was cooled to 0° C., treated with 10 ml crushed ice and the DMF was vacuumed off. The residue, in methylene chloride, was washed well with water and dried over magnesium sulphate. The oil resulting on evaporation, solidified on standing for a few days to give 1-(2-methoxyphenyl)-4-(1-oxo-2-phenoxy-2-phenylethyl)piperazine.

(c) 1-(2-Methoxyphenyl)-4-(1-oxo-2-phenoxy-2-phenylethyl)piperazine (3.77 g; 0.1 m) in dry THF (30 ml) was added to lithium aluminium hydride (1.5 g) in cold THF (100 ml) and the mixture refluxed for hours. After standing overnight the mixture was treated with ammonium chloride (1.56 g) in water (5 ml). The mixture was stirred for ½ hour and then filtered. The solid was washed with ethyl acetate and the combined filtrates evaporated to give an oil that was dissolved in ethanol and acidified with ethereal hydrogen chloride to give the title compound as the dihydrochloride (2.3 g), m.p. 196°–200° C. (Found C, 65.0;H,6.7;N,6.0. $C_{25}H_{28}N_2O_2$ requires C, 65.1;H,6.55; N 6.1%).

EXAMPLE 4

1-(2-Methoxyphenyl-1-4-[2-(3-methylphenoxy)-2-phenylethyl]piperazine

The title compound was obtained following the procedure of Example 3(c) by reduction of 1-2(methoxyphenyl-4-[1-oxo-2-(3-methylphenoxy)-2-phenylethyl]-piperazine which was prepared in a manner analogous to that of Example 3(a) and (b). The product was obtained as the dihydrochloride, half hydrate, m.p. 186°–189° C.

EXAMPLE 5

1 -(2-Methoxyphenyl)- 4-[(2-(4-fluorobenzyl)-2-pyridyl)ethyl]piperazine n-Butyllithium (1.6M solution in hexane) (9.00 ml, 14.4 mmol) was added dropwise at −70° C. to a solution of 1-(2-methoxyphenyl)-4-(2-[(4]-pyridyl)ethylpiperazine (4.010 g, 13.48 mmol) in anhydrous THF (40 ml). The solution was stirred for 0.25 h at −70° C. then treated dropwise with a solution of 4-fluorobenzyl chloride (2.10 g, 14.52 mmol) in THF (10 ml) at below −50° C. The mixture rapidly decolourised and was allowed to warm to 0° C., quenched with water (20 ml), and extracted with dichloromethane (1×75 ml, 2 ×25 ml). The extract was washed (brine; 20 ml), dried ($Na_2SO_4$), and concentrated in vacuo to give a brown oil (5.6 g). This was subjected to chromatography ($SiO_2$:$Et_2O$) to afford the product as a very pale yellow oil (4.23 g A sample of the base (1.535 g) was dissolved in ether (30 ml ), acidified with ethereal hydrogen chloride, and concentrated in vacuo to give a white solid. This was recrystallised from EtOH-EtOAC to afford the title compound as the dihydrochloride dihydrate, m.p. 133°–136° C. (Found: C,58.67; H,6.69; N,8.12.

$C_{25}H_{28}FN_3O \cdot 2HCl \cdot 2H_2O$ requires C,58.37; H,6.66; N,8.17%).

EXAMPLE 6

1-(2-Methoxyphenyl)-4-[(2-(4-fluorobenzyl)-2-methyl-2-(2-pyridyl)ethyl]piperazine A solution of n-butyllithium ( 9ml, 1.6M solution in hexane) was added dropwise to a solution of 1-(2-methoxyphenyl) -4-[2-(2-pyridyl )ethyl]piperazine (4.05 g, 13.6 mmol) in dry THF (80 ml) maintained at −70° C. After addition the solution was maintained at −70° C. for a further 0.5 h and then a solution of 4-fluorobenzyl chloride (1.96 g, 13.6 mmol]in dry THF (20 ml ) added at the same temperature. After stirring at −70° C. for 0.25 h a further 9ml of n-butyllithium was added followed 0.25 h later by iodomethane Cl ml). The reaction was allowed to rise to ambient temperature, quenched with brine (25 ml) and extracted with dichloromethane. The organic phase was dried, evaporated and the residue chromatographed on silica using 1:1 hexane-ether as eluent to give the title product (1.8 g). The base was dissolved in ethanol (20 ml) and acidified with ethanolic-HCl and diluted with ether to precipitate the crystalline dihydrochloride (1.5 g), m.p. 198°–200° C.

EXAMPLE 7

1-(2-Methoxyphenyl)-4-[3-(1H-imidazol-1-yl)-1-oxo-2-phenylpropyl]piperazine

Atropic acid (2.11 g, 0.01.4 m) suspended in dry dichloromethane (30 ml) was treated with 1,1-carbonyl diimidazole (2.31 g, 0.0142 m) over 10 minutes at ambient temperature and stirring was continued for 30 minutes. 2-Methoxyphenylpiperazine (2.76 g, 0.0143 m) was added and the mixture was stirred for 16–20 hrs. The solution was washed with water and the dichloromethane fraction was dried over magnesium sulphate. The residue was purified by dry column flash chromatography to give 1.46 g of product .

(b) 1-(2-Methoxyphenyl)4-[3-(1H-imidazol-1-yl)-2-phenylpropyl]piperazine

The above amide from part (a) (4.9 g, 0.01.25 m) was reduced in tetrahydrofuran using 1.0 g of lithium aluminium hydride. After 1 hr at 80° C. the mixture was cooled to 0°–5° C. and treated with (i) water (1 ml ); (ii 2N NaOH (2 ml) and (iii) water (1 ml) . The filtrate from the resulting mixture was evaporated and the residue was dissolved in chloroform. The chloroform solution was washed with water and dried over magnesium sulphate to give 4.3 g of an oil that was purified by dry column flash chromatography to give 2.0 g of pure title compound base. 1.6 g of this base was dissolved in ethanol and acidified with ethanolic hydrogen chloride. The residue on evaporation was crystallised from ethanol to give 0.7 g of the trihydrochloride salt, m.p. 201°–205° C.

EXAMPLE 8

1-(2-Methoxyphenyl)-4-[2-(4-fluorobenzyl)-2-(4-pyridyl)ethyl]piperazine 1-(2-Methoxyphenyl)-4-[2-(4-pyridyl)ethyl]piperazine (5.94 g, 20 mmol) was dissolved in anhydrous THF (70 ml) and the solution cooled to about −78° C., n-Butyllithium (1.6M solution in hexane, 18 ml) was added in portions, then the mixture was stirred for 1 hour, at below −70° C. The anion was quenched with p-fluorobenzylbromide (3.18 g, 16.8 mmol) in THF (3 ml and the mixture was warmed to room temperature when water (50 ml) was added. The organic component was extracted by dichloromethane, then washed with brine, dried using sodium sulphate and concentrated in vacuo. The resulting oil was purified by column chromatography using methanol:chloroform (0:100–5:95 gradient), affording the pure product. Addition of ethanolic HCl to the oil gave the title compound as the trihydrochloride 1.5 hydrate (1.25 g), m.p. 173°–175° C.

We claim:

1. A compound of the formula (I)

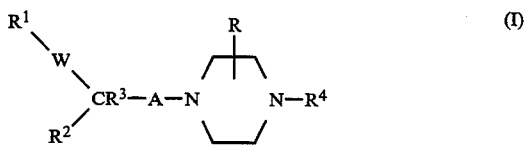

or a pharmaceutically acceptable acid addition salt thereof, wherein

W is $(CH_2)_m$, CHOH or O, m is one of the integers 1 or 2,

A is an alkylene chain of 1 to 3 carbon atoms optionally substituted by one or more (lower)alkyl groups, R is hydrogen or lower alkyl, $R^1$ and $R^2$ are each, independently, phenyl, naphthyl, pyridinyl, pyrimidinyl, pyrazinyl, imidazolyl, pyrazolyl, triazolyl or tetrazolyl each of which may be optionally substituted by one or more substituents selected from lower alkyl, lower alkoxy, halogen, halo(lower)alkyl, nitro, amino, (lower)alkylamino, di(lower)alkylamino, phenyl, halophenyl, (lower)alkylphenyl or (lower)alkoxyphenyl, $R^3$ is hydrogen or lower alkyl and $R^4$ is phenyl, naphthyl, pyridinyl, pyrimidinyl, pyrazinyl, quinolinyl, or isoquinolinyl each of which may be optionally substituted by one or more substituents selected from lower alkyl, lower alkoxy, halogen, halo(lower)alkyl, nitro, amino, (lower)alkylamino, di(lower)alkylamino, phenyl, halophenyl, (lower)alkylphenyl (lower)alkoxyphenyl, hydroxy, hydroxy(lower)alkyl, and —$CONR^5R^6$ (where $R^5$ and $R^6$ are each hydrogen, lower alkyl or —$NHSO_2$(lower)alkyl).

2. A compound of claim 1 wherein A is —$CH_2$—, —$CH_2CH_2$— or —$CH_2CH_2CH_2$—.

3. A compound as claimed in claim 1 wherein $R^4$ is optionally substituted by one or more substituents selected from lower alkyl, lower alkoxy, halogen, halo(lower)alkyl, nitro, amino, (lower)alkylamino, di(lower)alkylamino, phenyl, halophenyl, (lower)alkylphenyl or (lower)alkoxyphenyl.

4. A compound as claimed in claim 1 which is 1-(2-methoxyphenyl)-4-(2-phenoxy-2-phenylethyl)-piperazine or 1-(2-methoxyphenyl-4-[2-(3-methylphenoxy)-2-phenylethyl]piperazine or 1-(2- methoxyphenyl )-4-[2-(4-fluorobenzyl)-2-meth-yl-2-(2-pyridyl)ethyl]piperazine or 1-(2-methoxyphenyl)4-[(3-(1H-imidazol-1-yl)-2-phenylpropyl]piperazine or 1-(2-methoxyphenyl)-4-[2-(4-fluorobenzyl)-2-(4-pyridyl)ethyl]piperazine, or a pharmaceutically acceptable acid addition salt thereof.

5. A pharmaceutical composition comprising a compound of claim 1 in association with a pharmaceutically acceptable carrier.

6. A method of treating anxiety or depression in a mammal in need thereof, comprising administering to said mammal an amount of a compound of claim 1, or a pharmaceutically acceptable salt thereof, effective to alleviate anxiety or depression.

* * * * *